United States Patent
Schmitt

(10) Patent No.: US 7,458,986 B2
(45) Date of Patent: *Dec. 2, 2008

(54) SELF-EXPANDING STENT

(75) Inventor: Klaus Schmitt, Remshalden (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 69 days.

This patent is subject to a terminal disclaimer.

(21) Appl. No.: 11/334,639

(22) Filed: Jan. 17, 2006

(65) Prior Publication Data

US 2006/0142832 A1    Jun. 29, 2006

Related U.S. Application Data

(63) Continuation of application No. 10/423,136, filed on Apr. 24, 2003, now Pat. No. 7,387,641.

(30) Foreign Application Priority Data

Apr. 27, 2002   (DE)   ............................. 102 19 014

(51) Int. Cl.
*A61F 2/06*   (2006.01)
(52) U.S. Cl. .................... 623/1.22; 623/1.44
(58) Field of Classification Search ............. 623/1.22, 623/1.44, 1.13, 1.16
See application file for complete search history.

(56) References Cited

U.S. PATENT DOCUMENTS

| | | | | |
|---|---|---|---|---|
| 4,475,972 A | * | 10/1984 | Wong | 156/167 |
| 4,731,073 A | * | 3/1988 | Robinson | 623/1.44 |
| 4,743,252 A | * | 5/1988 | Martin et al. | 623/1.44 |
| 5,084,065 A | * | 1/1992 | Weldon et al. | 623/1.44 |
| 5,607,478 A | * | 3/1997 | Lentz et al. | 623/23.69 |
| 6,124,523 A | * | 9/2000 | Banas et al. | 623/1.15 |
| 6,156,064 A | * | 12/2000 | Chouinard | 623/1.44 |
| 6,162,244 A | * | 12/2000 | Braun et al. | 623/1.12 |
| 6,217,609 B1 | * | 4/2001 | Haverkost | 623/1.22 |
| 6,331,191 B1 | * | 12/2001 | Chobotov | 623/1.44 |
| 6,540,780 B1 | * | 4/2003 | Zilla et al. | 623/1.39 |
| 6,579,314 B1 | * | 6/2003 | Lombardi et al. | 623/1.44 |
| 6,622,604 B1 | * | 9/2003 | Chouinard et al. | 87/11 |
| 6,719,784 B2 | * | 4/2004 | Henderson | 623/1.44 |
| 6,939,337 B2 | * | 9/2005 | Parker et al. | 604/528 |
| 7,387,641 B2 | * | 6/2008 | Schmitt | 623/1.22 |
| 2001/0018609 A1 | * | 8/2001 | Smith | 623/1.13 |
| 2001/0049554 A1 | * | 12/2001 | Ruiz et al. | 623/1.44 |
| 2002/0096252 A1 | * | 7/2002 | Lukic | 156/294 |

FOREIGN PATENT DOCUMENTS

WO   WO 97/17039   *   5/1997

* cited by examiner

*Primary Examiner*—Corrine McDermott
*Assistant Examiner*—Cheryl Miller
(74) *Attorney, Agent, or Firm*—Hoffmann & Baron, LLP

(57) ABSTRACT

In an inventive stent (10), helical filaments (12, 13) are disposed on a first tubular layer (11). The helical filaments (12, 13) are mutually phase-shifted such that they do not touch and lie in one plane. The helical filaments (12, 13) are completely coated by a second elastic tubular polymer layer (14) which is connected to the first elastic tubular layer (11). Further helical filaments may be disposed on the second elastic tubular layer (14). The inventive stent can be lengthened for introduction into a hollow organ and is self-expanding.

15 Claims, 3 Drawing Sheets

SELF-EXPANDING STENT

This application is a continuation of U.S. Ser. No. 10/423,136, filed Apr. 24, 2003 now U.S. Pat. No. 7,387,641.

BACKGROUND OF THE INVENTION

The invention concerns a self-expanding stent for transluminal implantation into a hollow organ. Narrowed hollow organs can be splinted and/or kept open by means of a self-expanding stent.

A stent of this type is disclosed in the document EP 0 901 353 B1.

The known stent permits radial expansion of vessel narrowings as well as splinting or keeping them open. In its tapering and stretched state, the stent is introduced into a hollow organ and radially expanded at the narrowed location of the hollow organ to ensure that the hollow organ assumes its original lumen at this location if possible permanently. For self-expansion, meshworks are conventionally used which can be processed into stents. The meshworks can be lengthened against their load-free initial structure. If lengthening or radial deformation is released, these known stents return into their initial state through radial extension. This effect is used for widening stenoses in hollow organs to prevent their function from being impaired if possible.

SUMMARY OF THE INVENTION

It is the underlying purpose of the invention to develop a stent which can be designed to have a broad response characteristic with simple means and can be placed safely, permanently and undetachably in a hollow organ.

This object is achieved in accordance with the invention in that a self-expanding stent for splinting and/or keeping open a hollow organ consists of a first elastic tubular layer which supports one single first helical filament which is coated by a second elastic tubular layer which is connected in a material-bonding fashion at least at its ends with the first elastic tubular layer and fixes the position of the at least one helical filament.

The inventive self-expanding stent is thereby substantially advantageous in that meshworks can be omitted thereby still simultaneously permanently and securely keeping open sections of a hollow organ. A first helical filament is disposed onto a first elastic tubular layer, which consists e.g. of silicon, and whose inner surface may have a smooth and/or hydrophilic coating, wherein the filament is coated by a second elastic tubular layer, e.g. a silicon layer which keeps the helix permanently fixed in position on the first elastic tubular layer. The helix reinforces the elastic plastic layers and it is clear that the first and second elastic tubular layer can be produced from any medically harmless polymer. The helix ensures in a simple fashion, that the inventive stent does not collapse even under a certain radial pressure on the outer surface of the stent and permanently splints and keeps open the desired section of a hollow organ.

The first and second elastic tubular layers are connected to each other at least at the free ends of the inventive stent in a material-bonding fashion so that the helix disposed between the layers has a coating envelope in any state. The large flexibility of the helix between the layers can adjust the properties of the inventive stent via the resilient properties of the helix.

To increase the forces for expanding an inventive stent, it is advantageous to dispose several first helical filaments in a phase-shifted and mutually distanced fashion relative to other filaments in one plane on the first elastic tubular layer. All first helical elements are thereby in one plane (cylinder jacket surface). The phase-shifted first helical filaments do not touch another and are completely surrounded by the second elastic tubular layer which forms a material bond with the first elastic tubular layer. Desired restoring forces can be adjusted in a defined fashion via several phase-shifted first helical filaments.

Connection of the first and second elastic tubular layers over the entire length of the inventive stent in a material-bonding fashion ensures that the helix in the material bond cannot be displaced in places due to local pressures. The inventive stent forms a unit which results from specific cooperation of the two elastic tubular layers with the helix.

If the second elastic tubular layer has a thinner cross-section than the first or several first helical filaments, the structures of the helix project past the outer surface of the inventive stent producing a surface structure (topography) which keeps the inventive stent at the desired location of the hollow organ in a position which is as stable as possible.

If several first helical filaments are provided, they may have different cross-sections and/or diameters or heights/widths.

This is advantageous in that the expansion behavior of an inventive stent can be influenced through the simplest changes through cross-sectional changes to the helix. Circular, oval, triangular and square cross-sectional shapes are feasible for a helix and the most different cross-sections can be combined.

It is preferred that at least one helical filament is produced from plastic material, metal or carbon. The helical filaments moreover have the advantage that different materials can be combined in one material bond from which no meshworks, net or fabric can be produced. In the inventive stent, the helical filaments are disposed at a mutual separation in the material bond of the first and second elastic tubular layer and do not intersect. Helix of different materials can be combined and disposed in one plane.

In a further preferred embodiment of the inventive stent, the first and second elastic tubular layers have different elastic behavior and the layers consist of one or more polymers. This is advantageous in that the expansion behavior of the inventive stent can be influenced also via the first and second elastic tubular layer and be controlled in a defined manner. Important thereby are the material layers themselves and their properties under the influence of pressure, temperature and humidity.

If at least one second helical filament is disposed on the at least first helical filament, outside of a plane covered by the at least first helical filament, and if this second helical filament is coated with a third elastic tubular polymer layer, which is connected to the second elastic tubular layer, the inventive stent may be given further properties which meshworks cannot achieve. The second helical element lies in a second plane above the first helical filament and can have different material properties to the first helical filament. The second helical filament may have a larger or smaller separation from the first helical filament thereby completely changing the self-expanding behavior of the inventive stent compared to conventional self-expanding stents. If the inventive stent is lengthened, helical filaments having different diameters are stretched along a central longitudinal stent axis to different degrees so that material distortions can be produced in a precise fashion. This tension potential can be used for a desired expansion behavior and secure positioning.

In a further preferred embodiment, several second helical filaments are disposed on the at least one helical filaments in a phase-shifted fashion. This is advantageous in that the reinforcement or the flexibility of the inventive stent can be increased and additionally its outer surface properties can be adjusted to suit different applications through providing a more or less condensed layer of second helical filaments in one plane.

In an alternative embodiment the at least one second helical filament has a winding direction which is opposite to at least one first helical element. This frequently particularly suitable embodiment distorts the inventive stent during lengthening or stretching and this distortion is reversible so that the pre-distortion is returned during expansion and the inventive stent is turned into the inner surface of a hollow organ like a screw or abuts there.

Further advantages of an inventive stent are obtained when the several first and/or second helical filaments have different helix angles. Such embodiments produce manifold stent designs which are characterized by the most differing mechanical properties. The most different compression degrees and length extensions in different planes with different extents can be formed during lengthening and also expansion of a stent.

The expansion properties of the inventive stent are further supported when the third elastic tubular layer has a different thickness and/or different elastic behavior than the second elastic tubular layer. The third elastic tubular layer represents a further parameter which can be freely influenced and via which the self-expansion behavior of the inventive stent can be significantly influenced.

The inventive stent provides a self-expanding stent whose motion properties can be influenced via numerous controllable parameters in the simplest fashion. A multi-layer self-expanding stent with pre-shortening and pre-distortion can be produced, the inner surface of the inventive stent can be kept very smooth depending on the application and a first bundle of helical filaments does not influence the inner surface of the inventive stent since this bundle of helical filaments is supported on the outer surface of the first elastic tubular layer and does not have an effect on the surface of the inner surface or penetrates same. The first and/or second bundled helical filaments may abut to a stronger or weaker degree and be separated from each other, however, they do not intersect. The first and/or second helix may have different helix angles and the most different helix materials can be combined in each plane. The filaments may have different thicknesses and the tubular layers can also have different thicknesses. The first and second helical filaments may have varying separations (viewed in a radial direction) and the first helical filaments may be embedded into an elastic layer to an increased extent than the second helical filaments. If the second helical filaments are embedded in the third elastic tubular layer with less fixation, these second helical filaments are easier to protrude out of the outer surface of the third layer, and these second filaments may significantly mark the outer surface of the inventive stent.

Further advantages of the invention can be extracted from the description of the drawing which allows individual features in a highly schematized fashion. The illustrations in the figures are not to be taken to scale but rather have exemplary character.

DESCRIPTION OF THE PREFERRED EMBODIMENT

Figure 1:
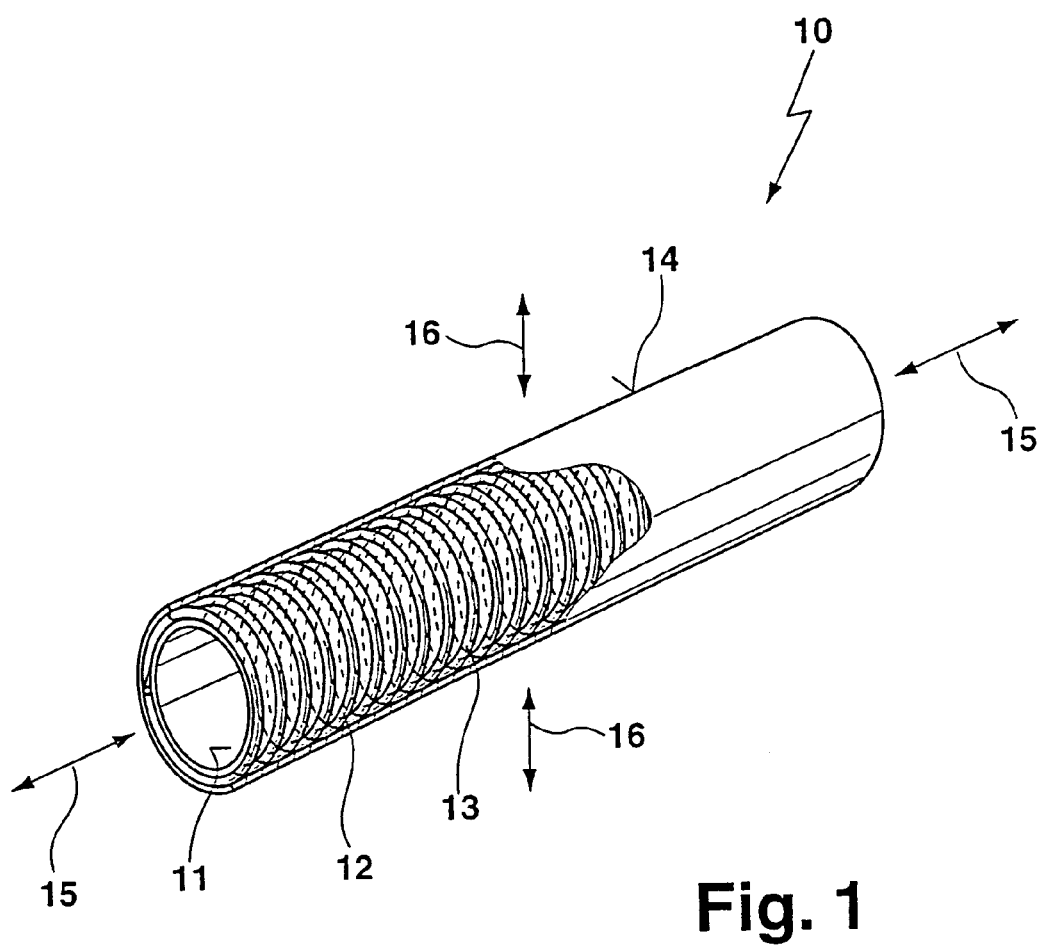
FIG. 1 shows a spatial representation of an inventive stent with phase-shifted first helical filaments.

In FIG. 1, 10 designates a stent which is composed of a first elastic tubular layer 11, a first helical filament 12, a phase-shifted first helical filament 13 and a second elastic tubular layer 14. The first helical filaments 12, 13 are in one plane at a mutual separation and do not intersect. Further first helical filaments may be embedded in the stent 10 if other stent designs are desired. If the inventive stent 10 is extended in the direction of arrows 15, the outer periphery of the stent 10 is tapered. If the forced lengthening of the stent 10 is released, the stent 10 expands itself and is enlarged in a radial direction in the direction of arrow 16 by shortening (contraction) and delimiting a larger lumen than in the tapered lengthened state. Several helical filaments are disposed in a helical and phase-shifted fashion onto a first elastic tubular layer 11 which is produced through a dipping method, and via further material coating, the first helical filaments 12, 13 are rigidly embedded into a polymer matrix, e.g. of silicon which is connected to the first elastic tubular layer 11 in a material bonding fashion. The second elastic tubular layer 14 may be produced from the same polymer material as the first elastic tubular layer 11. Both layer 11, 14 may have different thicknesses.

Figure 2:
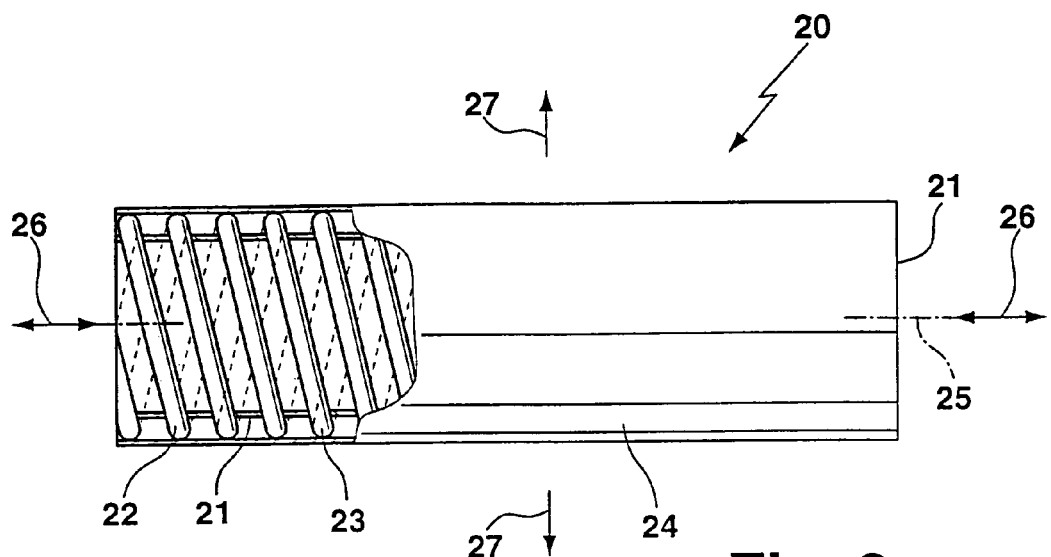
FIG. 2 shows a side view of a further inventive stent with phase-shifted first helical filaments.

FIG. 2 shows a side view of a further inventive stent 20. A first helical filament 22 of metal, carbon or plastic material is disposed onto a first elastic tubular layer 21 and a further first helical filament 23 is disposed phase-shifted thereto. The first helical filaments 22, 23 are completely coated with a second elastic tubular layer 24 which is material-bonded with the first elastic tubular layer 21. The first helical filaments 22, 23 have the same separation from a central axis 25 of the inventive stent 20 such that they are disposed in one plane. The stent 20 can be lengthened or shortened in the direction of arrows 26. The stent 20 is designed such that it contracts in a self-expanding fashion thereby enlarging in a radial direction. The stent 20 may taper or expand in the direction of arrows 27. The elastic tubular layers 21, 24 may have different material properties, different colours and one or both layers may be designed to provide X-ray shadow.

Figure 3:
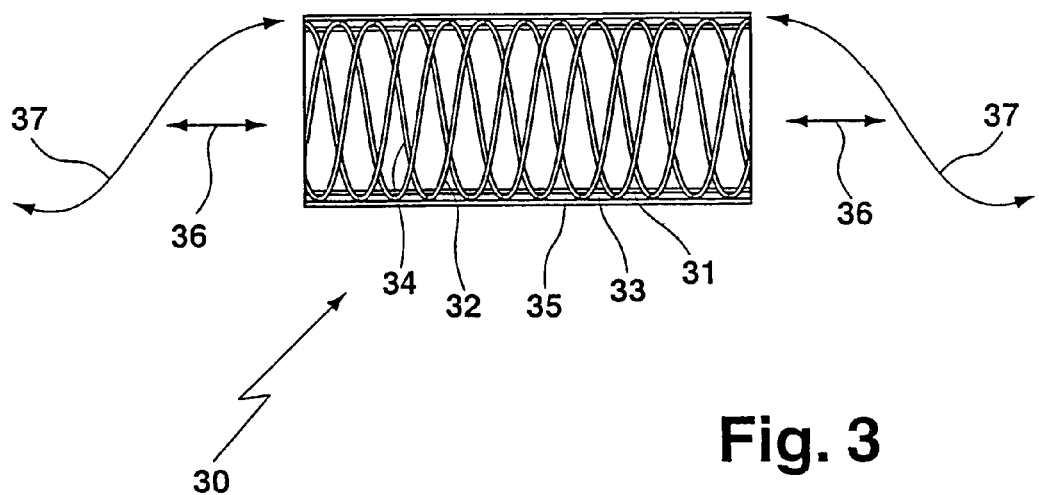
FIG. 3 shows a side view of an embodiment of an inventive stent with first and second helical filaments in different planes and with opposite winding directions between the first and second helical filament.

FIG. 3 shows a particularly advantageous embodiment of an inventive stent 30 which has a first helical filament 32 on a first elastic tubular layer 31. The first helical filament 32 is bonded via a second elastic tubular layer 33 to the first elastic tubular layer 31 and positionally fixed there. A second helical filament 34 is disposed on the first helical filament 32 and thereby on the second elastic tubular layer 33 outside of the plane of the first helical filament 32 which covers the first helical filament 32 at a radial separation. The second helical filament 34 is positionally fixed via a third elastic tubular layer 35 which is rigidly connected to the second elastic tubular layer 33. The second helical filament 34 has an opposite winding direction to the first helical filament 32 such that, when the stent 30 is lengthened, the stent 30 is distorted (twisted). If the stent 30 is lengthened in the direction of arrows 36, it is simultaneously twisted and tapered in the direction of arrows 37 (pre-distortion during stretching). The stent 30 consists of several layers and the helical filaments 32, 34 are disposed in different planes in the stent 30. In addition to the first and second helical filaments 32, 34 further phase-shifted first and second helical filaments may be embedded in the polymer matrix in each plane.

Figure 4:
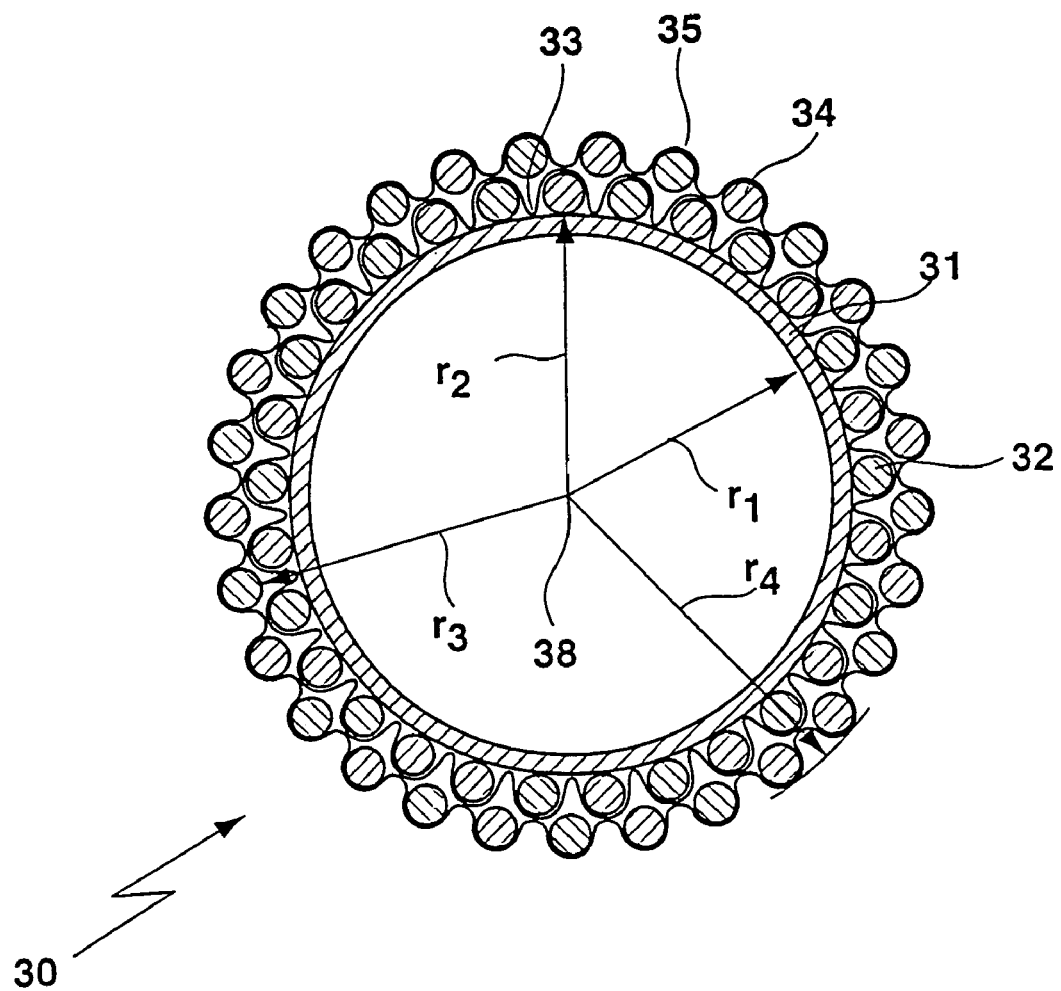
FIG. 4 shows a cross-section of a further embodiment of an inventive self-expanding stent with first phase-shifted helical filaments and second phase-shifted helical filaments with opposite winding directions.

FIG. 4 shows a cross-section through a stent in the expanded state with several first and second helical filaments. Viewed from a central axis 38 in the longitudinal direction of the stent, the first elastic tubular layer 31 is separated from the central axis 38 at a radius $r_1$. The first helical filaments 32 are disposed on the outer surface of the first elastic tubular layer 31 having a separation $r_2$ from the central axis 38. The first helical filaments 32 are surrounded by a second elastic tubular layer 33. Second helical filaments 34 are disposed on the first helical filaments 32 with opposite winding directions at a separation $r_3$ from the central axis 38. In the expanded state of the stent, the outer radius is $r_4$ which is delimited by a third elastic tubular layer 35 which surrounds the second helical filaments 34. $R_1 < r_2$, $r_2 < r_3$ and $r_3 < r_4$.

In an inventive stent 10, helical filaments 12, 13 are disposed on a first tubular layer 11. The helical filaments 12, 13 are mutually phase-shifted such that they do not touch another and are disposed in one plane. The helical filaments 12, 13 are completely coated by a second elastic tubular layer 14 which is connected to the first elastic tubular layer 11. The second elastic tubular layer 14 may comprise further helical filaments. The inventive stent can be lengthened for insertion into a hollow organ and expands itself.

I claim:

1. Self-expanding stent for splinting and/or keeping open a hollow organ, the stent comprising:
   a first elastic tubular layer;
   a first filament layer consisting essentially of several first nonintersecting helical filaments disposed in a phase-shifted fashion and a spaced apart relationship in one plane on the first elastic tubular layer, wherein the several first helical filaments do not intersect with any filaments in the one plane;
   a second elastic tubular layer coating the several first helical filaments, the second elastic tubular layer being connected at least at ends thereof with the first elastic tubular layer in a material-bonding fashion for fixing a position of the first helical filaments;
   a second filament layer comprising at least one second helical filament disposed on the first helical filaments outside of a plane spanned by the first helical filaments; and
   a third elastic tubular layer coating the at least one second helical filament, the third elastic tubular layer comprising a polymer connected to the second elastic tubular layer.

2. The stent according to claim 1, wherein the first and second elastic tubular layers are connected to one another over an entire length of the stent in a material-bonding fashion.

3. The stent according to claim 1, wherein a cross-section of the second elastic tubular layer is thinner than a cross-section of the first helical filaments.

4. The stent according to claim 1, wherein the first helical filaments have different cross-sections and/or diameters or height/widths.

5. The stent according to claim 1, wherein the first and second elastic tubular layers have different elastic properties and comprise one or more polymers.

6. The stent according to claim 1, further comprising several second helical filaments, wherein the several second helical filaments are disposed in a mutually phase-shifted fashion on the first helical filaments.

7. The stent according to claim 1, wherein the at least one second helical filament has a winding direction which is opposite to a winding direction of the first helical filaments.

8. The stent according to claim 1, further comprising several second helical filaments, wherein the second helical filaments are coated with the third elastic tubular layer.

9. Self-expanding stent for splinting and/or keeping open a hollow organ, the stent comprising:
   a first elastic tubular layer;
   a filament layer consisting essentially of several first helical filaments disposed in a phase-shifted fashion and a spaced apart relationship in one plane on the first elastic tubular layer, wherein the several first helical filaments in the one plane of the filament layer are nonintersecting filaments;
   a second elastic tubular layer coating the several first helical filaments, the second elastic tubular layer being connected at least at ends thereof with the first elastic tubular layer in a material-bonding fashion for fixing a position of the several first helical filaments;
   at least one second helical filament disposed above the several first helical filaments outside of the one plane spanned by the several first helical filaments; and
   a third elastic tubular layer coating the at least one second helical filament, the third elastic tubular layer comprising a polymer connected to the second elastic tubular layer.

10. The stent according to claim 9, wherein the first and second elastic tubular layers are connected to one another over an entire length of the stent in a material-bonding fashion.

11. The stent according to claim 9, wherein a cross-section of the second elastic tubular layer is thinner than a cross-section of the first helical filaments.

12. The stent according to claim 9, wherein the first helical filaments have different cross-sections and/or diameters or height/widths.

13. The stent according to claim 9 wherein the first and second elastic tubular layers have different elastic properties and comprise one or more polymers.

14. The stent according to claim 9 further comprising several second helical filaments, wherein the several second helical filaments are disposed in a mutually phase-shifted fashion on the first helical filaments.

15. The stent according to claim 9 wherein the at least one second helical filament has a winding direction which is opposite to a winding direction of the first helical filaments.

* * * * *